United States Patent [19]
Enokida et al.

[11] Patent Number: 5,744,640
[45] Date of Patent: Apr. 28, 1998

[54] FLUORINE RUBBER COMPOSITION

[75] Inventors: Takashi Enokida; Akihiro Naraki; Eiichi Yamashita, all of Kitaibaraki; Haruyoshi Tatsu, Hitachi, all of Japan

[73] Assignee: Nippon Mektron, Limited, Tokyo, Japan

[21] Appl. No.: 714,192

[22] Filed: Sep. 16, 1996

Related U.S. Application Data

[62] Division of Ser. No. 583,642, Jan. 5, 1996, Pat. No. 5,587,413.

[30] Foreign Application Priority Data

Jan. 13, 1995 [JP] Japan ................................. 7-021359

[51] Int. Cl.$^6$ .................... C07C 271/60; C07C 275/30; C07C 275/08; C07C 275/14
[52] U.S. Cl. ........................... 564/51; 564/59; 564/255
[58] Field of Search .......................... 564/51, 59, 255

[56] References Cited

U.S. PATENT DOCUMENTS 3,398,182  8/1968  Guenthner et al. .
5,252,689  10/1993  Lucas ........................................ 526/227

FOREIGN PATENT DOCUMENTS

| 53-112855 | 2/1978 | Japan . |
|---|---|---|
| 131687 | 10/1981 | Japan . |
| 57-29584 | 6/1982 | Japan . |
| 105097 | 6/1984 | Japan . |
| 105098 | 6/1984 | Japan . |
| 109574 | 6/1984 | Japan . |
| 109575 | 6/1984 | Japan . |
| 2-209984 | 8/1990 | Japan . |

OTHER PUBLICATIONS

Oertel *Polyurethane Handbook* p. 20; 1993.

*Primary Examiner*—David Buttner
*Attorney, Agent, or Firm*—Barnes & Thornburg

[57] ABSTRACT

A fluorine rubber composition comprising a fluorine rubber and a polyfluoroalkyl group-containing block isocyanate compound represented by the following general formula:

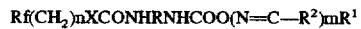

$$Rf(CH_2)_nXCONHRNHCOO(N=C-R^2)_mR^1$$

where Rf is a polyfluoroalkyl group having 4 to 20 carbon atoms; R is a divalent organic group; $R^1$ is a lower alkyl group or phenyl group; $R^2$ is a lower alkyl group; X is NH or O; n is an integer of 1 to 4 and m is 0 or 1, has a good vulcanization bond to metals without any substantial decrease in the rubber stretchability properly owned by the fluorine rubber.

1 Claim, No Drawings

FLUORINE RUBBER COMPOSITION

This a Divisional of application Ser. No. 08/583,642 filed Jan. 5, 1996, now U.S. Pat. No. 5,587,413.

BACKGROUND OF THE INVENTION

1. Field of the Invention

The present invention relates to a fluorine rubber composition, more particularly to a fluorine rubber composition having a good vulcanization bond to metals, etc.

2. Related Prior Art

Vulcanized fluorine rubber has good heat resistance, chemical resistance, oil resistance, weathering resistance, etc., and thus has been so far widely used as sealing materials in the form of gaskets, O-rings, oil seals, packings, etc. in the fields of the automobile industry, oil hydraulic industry, general mechanical industry, aircraft industry, etc.

Particularly the sealing materials for making oil seals, gaskets, etc. require a good vulcanization bond between the fluorine rubber and metals, and for this purpose it is the usual practice to apply a silane coupling agent to a phosphate-coated mild steel plate, followed by baking and then to provide an unvulcanized fluorine rubber compound thereon, followed by pressure vulcanization.

As to the improvement of vulcanization bondability of fluorine rubber to metals, JP-A-3-37251 discloses a fluorinated elastomer composition comprising a terpolymer elastomer gum of vinylidene fluoride-tetrafluoroethylene-hydrocarbon olefin, a polyhydroxy compound, an organic onium compound and a fluoro-substituted aliphatic sulfonyl compound as a bonding promoter, where polyfluoroalkyl-N-substituted sulfonamide, represented by the general formula $RfSO_2NHR$, etc. are used as a fluoro-substituted aliphatic sulfonyl compound as a bonding promoter.

However, the polyfluoroalkyl-N-substituted sulfonamide, etc. as a bonding promoter for bonding a fluorine rubber to metals have given a satisfactory bond yet. An increase in the amount of the bonding promoter to enhance their bondability has considerably lowered the stretchability and no satisfactory rubber stretchability has been obtained. In the polyol vulcanization of fluorine rubber, the polyfluoroalkyl-N-substituted sulfonamide, etc. have a lower vulcanization rate problem and also have a restricted freedom of compounding design.

SUMMARY OF THE INVENTION

An object of the present invention is to provide a fluorine rubber composition with an improved bondability to metals, etc. without any substantial decrease in the rubber stretchability properly owned by fluorine rubber.

According to the present invention, there is provided a fluorine rubber composition which comprises a fluorine rubber and a polyfluoroalkyl group-containing block isocyanate compound represented by the following general formula:

$Rf(CH_2)nXCONHRNHCOO(N=C—R^2)mR^1$ where Rf is a polyfluoroalkyl group having 4 to 20 carbon atoms; R is a divalent organic group; $R^1$ is a lower alkyl group or phenyl group; $R^2$ is a lower alkyl group; X is NH or O; n is an integer of 1 to 4; and m is 0 or 1.

DETAILED DESCRIPTION OF THE INVENTION

In the present invention, a vinylidene fluoride-hexafluoropropene copolymer containing about 10 to about 30% by mole, preferably about 15 to about 25% by mole, of hexafluoropropene, as copolymerized, or a vinylidene fluoride-hexafluoropropene-tetrafluoroethylene terpolymer containing about 5 to about 25% by mole, preferably about 15 to about 20% by mole, of hexafluoropropene and about 0.1 to about 35% by mole, preferably about 5 to about 25% by mole, of tetrafluoroethylene, as copolymerized, is preferably used as a fluorine rubber for bonding to metals, etc. Besides, a tetrafluoroethylene-propylene copolymer, a tetrafluoroethylene-perfluoro-(methyl vinyl ether) copolymer, a tetrafluoroethylene-vinylidene fluoride-perfluoro(methyl vinyl ether) terpolymer, a vinylidene fluoride-chlorotrifluoroethylene copolymer, etc. can be also used in the present invention.

These fluorine rubbers are amine-vulcanizable, polyol-vulcanizable or peroxide-vulcanizable in the presence of a cocross-linking agent. All these vulcanization procedures are well known, where appropriate cross-linking agents are each used according to the respective vulcanization procedures. That is, cross-linking agents for the amine vulcanization include, for example, 4,4'-methylenebis(cyclohexylamine) carbamate, hexamethylenediamine carbamate, N,N'-dicinnamylidene-1,6-hexadiamine, etc. Cross-linking agents for the polyol vulcanization includes, for example, polyhydroxy aromatic compounds such as 2,2-bis(4-hydroxyphenyl)propane [bisphenol A], 2,2-bis(4-hydroxyphenyl)perfluoropropane [bisphenol AF], hydroquinone, catechol, resorcinol, 4,4'-dihydroxydiphenyl, 4,4'-dihydroxydiphenylmethane, 4,4'-dihydroxydiphenylsulfone, 2,2-bis(4-hydroxyphenyl) butane, etc., or their alkali metal or alkaline earth metal salts. About 0.5 to about 10 parts by weight, preferably about 1 to about 5 parts by weight, of the cross-linking agent is used per 100 parts by weight of the fluorine rubber. Any ordinary cooross-linking agent and any ordinary organic peroxide can be used for the peroxide vulcanization, so long as they are usually used in the peroxide vulcanization. About 0.5 to about 10 parts by weight, preferably about 0.5 to about 6 parts by weight, of the cocross-linking agent is used per 100 parts by weight of the fluorine rubber, and about 0.1 to about 5 parts by weight, preferably about 0.5 to about 3 parts by weight, of the organic peroxide is used per 100 parts by weight of the fluorine rubber.

When a polyhydroxyaromatic compound or its metal salt is used as a cross-linking agent, about 0.1 to about 10 parts by weight, preferably about 0.1 to about 2 parts by weight, of various quaternary ammonium salts or quaternary phosphonium salts are used as a vulcanization promoter per 100 parts by weight of the fluorine rubber. Furthermore, about 1 to about 20 parts by weight, preferably about 3 to about 15 parts by weight, of various oxides or hydroxides of divalent metals are used as an acid receptor per 100 parts by weight of the fluorine rubber.

Vulcanization bond of fluorine rubber to metals, etc. can be considerably improved by adding a polyfluoroalkyl group-containing block isocyanate compound to a fluorine rubber.

Among the polyfluoroalkyl group-containing block isocyanate compounds for use in the present invention, the compound whose m is zero and whose X is zero, i.e. $Rf(CH_2)nOCONHRNHCOOR^1$, is well known and is used as a water or oil repellent, a fiber processing agent or an anti-fouling agent (JP-A-2-209984; JP-B-57-29584; JP-B-59-23302; U.S. Pat. No. 3,398,182). However, it is not expectable at all from these known uses that the polyfluoroalkyl group-containing block isocyanate compound can effectively improve the vulcanization bond of fluorine rubber to metals, etc.

The divalent organic group R of the polyfluoroalkyl group-containing block isocyanate compound is residues derived from the following diisocyanate compounds having the general formula R(NCO)$_2$:

R(NCO)$_2$: 2,4-tolylene diisocyanate
4,4'-diphenylmethane diisocyanate
tolidine diisocyanate
dianisidine diisocyanate
2-methylcyclohexane-1,4-diisocyanate
isophorone diisocyanate
hydrogenated 4,4'-diphenylmethane diisocyanate
hexamethylene diisocyanate
decamethylene diisocyanate etc.

The polyfluoroalkyl group Rf is preferably such perfluoroalkyl groups as perfluorohexyl, perfluoroheptyl, perfluorooctyl, perfluorodecyl, perfluorododecyl, etc. Fluorine atoms, usually terminal fluorine atoms of these perfluoroalkyl groups can be replaced with hydrogen atoms, chlorine atoms, etc. Furthermore, these polyfluoroalkyl groups can be a mixture of the groups having various numbers of carbon atoms. R$^1$ is a lower alkyl group having not more than 5 carbon atoms or phenyl group.

The one whose m is 1 and whose X is NH, i.e. Rf(CH$_2$)nNHCONHRNHCOON=CR$^1$R$^2$, is a novel compound and can be prepared by the following series of reactions:

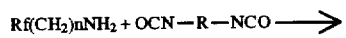

In the polyfluoroalkyl group-containing block isocyanate compounds prepared according to these reactions, the divalent organic group R and the terminal polyfluoroalkyl group Rf on one side are the above-mentioned groups, respectively, whereas the terminal group ON=CR$^1$R$^2$ on the other side can be derived from an isocyanate group and oximes. Oximes include, for example, acetoxime, methyl ethyl ketoxime, methyl isobutyl ketoxime, diisobutyl ketoxime, etc. whose R$^1$ and R$^2$ each are lower alkyl groups having not more than 5 carbon atoms.

As the polyfluoroalkyl group-containing block isocyanate compound, the compounds represented by the following general formula:

can be used in the present invention, where Rf, X and R have the same meanings as defined above, and R$^3$ is a alcohol-based compound residue, an active methylene-based compound residue, a mercaptane-based compound residue, an acid amide-based compound residue, an imide-based compound residue, an amine-based compound residue, an imine-based compound residue, an imidazole-based compound residue, a urea-based compound residue, a carbamate-based compound residue, a sulfite-based compound residue or an oxime-based compound residue.

About 0.05 to about 1 parts by weight, preferably about 0.05 to about 0.5 parts by weight, of the polyfluoroalkyl group-containing block isocyanate compound is used as a bonding promoter per 100 parts by weight of the fluorine rubber. Below the lower limit any desired bond strength cannot be obtained between the fluorine rubber and metals, whereas a satisfactory bond strength can be obtained below the upper limit, that is, use of the bonding promoter above the upper limit is not economically preferable.

The present fluorine rubber composition can contain at least one of carbon black, silica, graphite, clay, talc, diatomaceous earth, barium sulfate, titanium oxide, etc. as a filler or a reinforcing agent, or other necessary additives and can be prepared by kneading by an ordinary kneading means such as mixing rolls, etc. In the preparation, it is preferable to add a cross-linking agent such as bisphenol AF, etc. at a later stage.

Vulcanization of the thus prepared composition is carried out usually by press vulcanization (primary vulcanization) and oven vulcanization (secondary vulcanization) after the fluorine rubber composition is applied to a metal, preferably a primered metal. Injection molding is also possible for this purpose.

Addition of a polyfluoroalkyl group-containing block isocyanate compound to a fluorine rubber as a bonding promoter can considerably improve the vulcanization bond of the fluorine rubber to metals, etc. without any decrease in the stretchability and vulcanization rate, as compared with addition of polyfluoroalkyl-N-substituted sulfonamide in the same proportion.

PREFERRED EMBODIMENTS OF THE INVENTION

The present invention will be described in detail below, referring to Examples.

REFERENCE EXAMPLE 1

4.35 g (25 millimoles) of 2,4-tolylene diisocyanate and 50 g of dry acetone were charged into a 4-necked flask having a net capacity of 200 ml, provided with a thermometer, a dropping funnel with a pressure-equalizer pipe, a cooler and a vacuum stirrer and mounted on a mantle heater, and the air inside the flask was replaced with a dry nitrogen gas after the start of stirring. Then, 9.975 g (25 millimoles) of perfluoroheptylamine, C$_7$F$_{15}$CH$_2$NH$_2$, was dropwise added to the flask over about 30 minutes.

After the dropwise addition, stirring was continued for further 30 minutes, and then 2.175 g (25 millimoles) of methyl ethyl ketoxime, MeEtC=N—OH, was dropwise added thereto over about 15 minutes. After the end of heat release due to the dropwise addition, the liquid temperature was elevated up to 50° C. and the reaction was kept to continue for further 10 hours. After extinguishment of absorption of isocyanate group (2,250 cm$^{-1}$) was confirmed by infrared absorption spectrum of the reaction mixture, the liquid temperature was returned to room temperature.

After evaporation of volatile matters from the reaction mixture, the residual acetone was completely removed therefrom under reduced pressure at 50° C., whereby 16.0 g of white solid was obtained. 5.0 g of the white solid was subjected to development and separation by thin layer chromatography, whereby 3.5 g of polyfluoroalkyl group-containing block isocyanate compound [I] was obtained. Selectivity to the compound [I] was found to be 73% by high speed liquid chromatographic analysis of the white solid.

Melting point: 159°–161° C.

Elemental analysis (C$_{21}$H$_{19}$O$_3$F$_{15}$N$_3$):

Found: C; 38.01%, H; 2.84%, F; 43.25%, N; 8.55%
Calculated: C; 38.18%, H; 2.88%, F; 43.18%, N; 8.48%

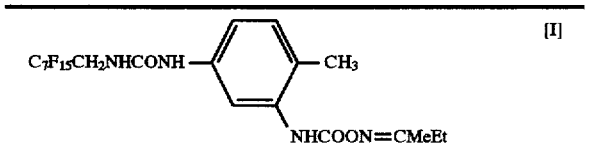

¹H-NMR

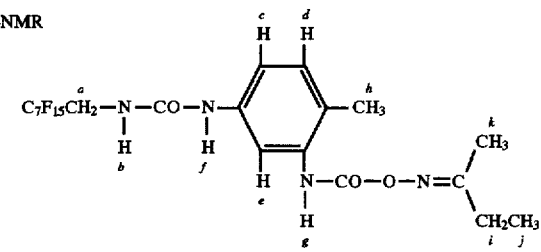

| Location | Chemical Shift (ppm) | Integrated intensity | Splitting |
|---|---|---|---|
| a | 4.00 | 2H | m |
| b | 5.26 | 1H | t |
| c–e | 7.10–7.80 | 3H | m |
| f–g | 8.24–8.35 | 2H | s |
| h | 2.25 | 3H | s |
| i | 2.40 | 2H | m |
| j | 1.19 | 3H | t |
| k | 1.51 | 3H | s |

(Measurement conditions)
Apparatus: type JEOL EX-270
Solvent: $CDCl_3$ (40° C.)
Standard substance: Tetramethylsilane
Number of integration: 64 runs

REFERENCE EXAMPLE 2

Polyfluoroalkyl group-containing block isocyanate compound [II] represented by the following formula was synthesized according to the procedure disclosed in JP-B-57-29584:

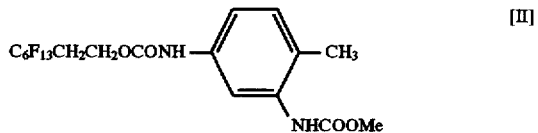

EXAMPLE 1

The following components were kneaded in 8-inch mixing rolls:

| Components | Parts by weight |
|---|---|
| Fluorine rubber A | 100 |
| Copolymer of vinylidene fluoride-hexafluoropropene in a molar ratio of 78:22 | |
| MT carbon black | 20 |
| Lead oxide (PbO) | 15 |
| 4,4'-methylenebis(cyclohexylamine) carbamate | 2 |
| Block isocyanate compound [I] of | 0.1 |

Then, the kneaded mixture was subjected to press vulcanization at 180° C. for 5 minutes and then to oven vulcanization at 230° C. for 22 hours, and the thus obtained vulcanization product was subjected to the following determinations:

Physical properties according to JIS K-6301
Compression set by 25% compression of P-24 O-ring at 200° C. for 70 hours Bondability to metal by applying a primer consisting of a 20 wt. % solution of a commercially available adhesive (AP-133, trademark of a product of Japan Unicar K. K., Japan) in methanol to a phosphate-coated mild steel plate, followed by leaving it at room temperature for 30 minutes for air drying; baking the dried plate at 150° C. for 10 minutes; then applying the kneaded mixture, followed by press vulcanization at 180° C. for 5 minutes; peeling the rubber layer from the metal-fluorine rubber bonding product with pliers, while measuring a percentage of the residual rubber area on the metal surface as an indicator for the bondability to metal.

EXAMPLE 2

In Example 1, the same amount of the block isocyanate compound [II] of Reference Example 2 was used in place of the block isocyanate compound [I] of Reference Example 1.

COMPARATIVE EXAMPLE 1

In Example 1, no block isocyanate compound [I] was used.

Results of determinations in Example 1 and 2 and Comparative Example 1 are shown together in the following Table 1.

TABLE 1

| Measurement Item | | Ex. 1 | Ex. 2 | Comp. Ex. 1 |
|---|---|---|---|---|
| Hardness | (JIS A) | 70 | 71 | 70 |
| 100% Modulus | (MPa) | 3.5 | 3.7 | 3.6 |
| Tensile strength | (MPa) | 15.9 | 16.1 | 16.2 |
| Elongation | (%) | 280 | 280 | 280 |
| Compression set | (%) | 51 | 52 | 50 |
| Bondability to metal (Residual rubber area, %) | | 100 | 100 | 60 |

EXAMPLE 3

The following components were kneaded, vulcanized and subjected to determinations in the same manner as in Example 1.

| Components | Parts by weight |
|---|---|
| Fluorine rubber B | 100 |
| Terpolymer of vinylidene fluoride-hexafluoropropene-tetrafluoroethylene in a molar ratio of 68:16:16 | |
| MT carbon black | 20 |
| Lead oxide (PbO) | 5 |
| Triallyl isocyanurate | 5 |
| TAIC M-60, trademark of a product made by Nihon Kasei K. K., Japan | |
| Organic peroxide | 2 |
| Perhexa 25B-40, trademark of a product of Nihon Yushi K. K., Japan | |
| Block isocyanate compound [I] of | 0.1 |

EXAMPLE 4

In Example 3, the same amount of the block isocyanate compound [II] of Reference Example 2 was used in place of the block isocyanate compound [I] of Reference Example 1.

COMPARATIVE EXAMPLE 2

In Example 3, no block isocyanate compound [I] was used.

Results of determinations in Example 3 and 4 and Comparative Example 2 are shown in the following Table 2.

TABLE 2

| Measurement Item | | Ex. 3 | Ex. 4 | Comp. Ex. 2 |
|---|---|---|---|---|
| Hardness | (JIS A) | 75 | 74 | 74 |
| 100% modulus | (MPa) | 6.3 | 6.5 | 6.3 |
| Tensile strength | (MPa) | 20.5 | 21.0 | 2.03 |
| Elongation | (%) | 218 | 220 | 220 |
| Compression set | (%) | 33 | 34 | 31 |
| Bondability to metal (Residual rubber area, %) | | 100 | 100 | 50 |

EXAMPLES 5 TO 8

The following components were kneaded, vulcanized and subjected to determinations in the same manner as in Example 1.

| Components | Parts by weight |
|---|---|
| Fluorine rubber A | 100 |
| MT carbon black | 25 |
| Calcium hydroxide | 5 |
| Magnesium oxide | 3 |
| Bisphenol AF | 2 |
| Benzyltriphenylphosphonium chloride | 0.4 |
| Block isocyanate compound [I] of Reference Example 1 | |
| (Example 5) | 0.05 |
| (Example 6) | 0.1 |
| (Example 7) | 0.3 |
| (Example 8) | 0.5 |

Furthermore, vulcanization was carried out at 180° C. for 10 minutes with an oscilating disc rheometer, type ASTM-100, made by Toyo Seiki K. K., Japan to measure the time (min.) until 90% of the maximum torque (tc 90) was obtained.

COMPARATIVE EXAMPLE 3

In Example 5, the same amount of perfluorooctyl-N-methyl-sulfonamide was used in place of the block isocyanate compound [I] of Reference Example 1.

COMPARATIVE EXAMPLE 4

In Example 6, the same amount of perfluorooctyl-N-methyl-sulfonamide was used in place of the block isocyanate compound [I] of Reference Example 1.

Results of determinations in Examples 5 to 8 and Comparative Examples 3 and 4 are shown in the following Table 3.

TABLE 3

| Measurement Item | | Example | | | | Comp. Ex. | |
|---|---|---|---|---|---|---|---|
| | | 5 | 6 | 7 | 8 | 3 | 4 |
| Hardness | (JIS A) | 69 | 70 | 69 | 70 | 69 | 70 |
| 100% modulus | (MPa) | 4.9 | 5.0 | 4.8 | 5.1 | 5.2 | 5.4 |
| Tensile strength | (MPa) | 14.0 | 14.2 | 13.8 | 13.1 | 14.9 | 15.3 |
| Elongation | (%) | 230 | 230 | 230 | 220 | 200 | 200 |
| Compression set | (%) | 21 | 21 | 23 | 23 | 19 | 20 |
| Bondability to metal (Residual rubber area, %) | | 90 | 100 | 100 | 100 | 70 | 80 |
| tc 90 | (min.) | 5.1 | 5.0 | 5.2 | 5.1 | 5.3 | 5.8 |

As is obvious from the foregoing results, addition of a polyfluoroalkyl group-containing block isocyanate compound as bonding accelerator to a fluorine rubber can considerably improve the vulcanization bond without any decrease in the stretchability and vulcani-zation rate, as compared with addition of polyfluoroalkyl-N-substituted sulfonamide in the same proportion.

What is claimed is:

1. A polyfluoroalkyl group-containing block isocyanate compound represented by the following general formula:

$$Rf(CH_2)_nNHCONHRNHCOON=CR^1R^2$$

where Rf is a polyfluoroalkyl group having 4 to 20 carbon atoms; R is a divalent organic group; $R^1$ is a lower alkyl group or a phenyl group; $R^2$ is a lower alkyl group and n is an integer of 1 to 4.

* * * * *